United States Patent
Ignatyev et al.

(10) Patent No.: US 8,211,277 B2
(45) Date of Patent: Jul. 3, 2012

(54) COMPOUNDS CONTAINING ORGANOFLUOROCHLOROPHOSPHATE ANIONS

(75) Inventors: Nikolai Ignatyev, Duisburg (DE); German Bissky, Hamm (DE); Helge Willner, Muelheim/Ruhr (DE)

(73) Assignee: Merck Patent GmbH, Darmstadt (DE)

( * ) Notice: Subject to any disclaimer, the term of this patent is extended or adjusted under 35 U.S.C. 154(b) by 320 days.

(21) Appl. No.: 12/525,099

(22) PCT Filed: Dec. 7, 2007

(86) PCT No.: PCT/EP2007/010646
§ 371 (c)(1), (2), (4) Date: Jul. 30, 2009

(87) PCT Pub. No.: WO2008/092489
PCT Pub. Date: Aug. 7, 2008

(65) Prior Publication Data
US 2010/0004461 A1    Jan. 7, 2010

(30) Foreign Application Priority Data

Jan. 31, 2007 (DE) .................. 10 2007 004 698

(51) Int. Cl.
C25B 9/00 (2006.01)
H01G 9/02 (2006.01)
H01M 6/04 (2006.01)
H01M 6/16 (2006.01)
C07D 233/61 (2006.01)
C07D 233/54 (2006.01)
C07D 233/64 (2006.01)
C07F 9/02 (2006.01)

(52) U.S. Cl. ....... 204/242; 252/62.2; 429/328; 429/188; 548/335.1; 548/343.1; 562/820

(58) Field of Classification Search ............... 548/335.1, 548/343.1; 562/820; 204/242; 252/62.2; 429/328, 188
See application file for complete search history.

(56) References Cited

U.S. PATENT DOCUMENTS

| | | | |
|---|---|---|---|
| 6,340,716 | B1 | 1/2002 | Armand et al. |
| 7,153,974 | B2 | 12/2006 | Schmidt et al. |
| 2002/0015884 | A1 | 2/2002 | Schmidt et al. |
| 2008/0194831 | A1 | 8/2008 | Ignatyev et al. |

FOREIGN PATENT DOCUMENTS

| | | |
|---|---|---|
| CA | 2 280 938 | 4/1998 |
| EP | 0 929 558 | 1/2001 |
| EP | 1 162 204 | 12/2001 |
| WO | WO-98/15562 | 4/1998 |
| WO | WO-02/085919 | 10/2002 |
| WO | WO-2006/128563 | 12/2006 |

OTHER PUBLICATIONS

Dillon et al., Journal of the Chemical Society, Chemical Communications (1983), (19), 1089-90.*
International Search Report for PCT/EP2007/010646 dated Apr. 16, 2008.
Ivanov, A. N. et al., "2,2,3,3-Tetrafluoropropyldichlorophosphite in the Allen reaction with 1,1-dichloro-1-nitrosoalkanes," J. Fluorine Chem., 1992, Bd. 58, Nr. 2-3, pp. 374, XP002470493.
Thomson Innovation, English Translation of Claims and Description retrieved from Thomson Innovation Record View on Jul. 28, 2010; English Abstract of WO2002085919.

* cited by examiner

*Primary Examiner* — Rebecca Anderson
(74) *Attorney, Agent, or Firm* — Millen, White, Zelano & Branigan, P.C.

(57) ABSTRACT

The present invention relates to compounds containing organofluorochlorophosphate anions, the preparation thereof and the use thereof, in particular as ionic liquids.

27 Claims, No Drawings

COMPOUNDS CONTAINING ORGANOFLUOROCHLOROPHOSPHATE ANIONS

The present invention relates to compounds containing organofluorochlorophosphate anions, the preparation thereof and the use thereof, in particular as ionic liquids.

Ionic liquids or liquid salts are ionic species which consist of an organic cation and a generally inorganic anion. They do not contain any neutral molecules and usually have melting points below 373 K.

The area of ionic liquids is currently being researched intensively since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227.

The properties of ionic liquids, for example melting point, thermal and electrochemical stability, viscosity, are strongly influenced by the nature of the anion. On the other hand, the polarity and hydrophilicity or lipophilicity can be varied through a suitable choice of the cation/anion pair. There is therefore a basic demand for novel ionic liquids having varied properties which facilitate additional potential uses.

EP 0 929 558, WO 02/085919 and EP 1 162 204 disclose salts containing perfluoroalkylfluorophosphate anions (FAP anions for short). These salts are distinguished by high electrochemical and thermal stability and at the same time have low viscosity. Salts based on FAP anions are substantially inert and have greater stability to hydrolysis than, for example, salts containing $PF_6^-$ anions.

However, it is often desired to have available compounds, for example as reaction medium, which can be decomposed easily after the reaction has been carried out in order to reduce the environmental pollution with compounds of very low biodegradability.

There was thus a demand for novel compounds which can be employed, for example, as ionic liquids and at the same time have easier degradability.

The object of the present invention is accordingly the provision of novel compounds which are suitable, for example, as ionic liquids.

The present object is achieved by the compounds according to the invention, processes for the preparation thereof and the use thereof.

The present invention thus relates firstly to compounds containing organofluorochlorophosphate anions, preferably salts containing organofluorochlorophosphate anions. For the purposes of the present invention, "organo" means any organic radical, for example aliphatic or aromatic organo radicals, which may in turn themselves be substituted, for example by further organo radicals or radicals containing heteroatoms. For the purposes of the present invention, there is no restriction regarding the organo radicals.

In particular, the compounds in accordance with the present invention are those of the formula (I)

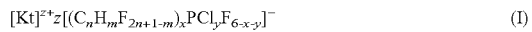
$$[Kt]^{z+}{}_z[(C_nH_mF_{2n+1-m})_xPCl_yF_{6-x-y}]^- \qquad (I)$$

in which $[Kt]^{z+}$ denotes an inorganic or organic cation, where n=1-12, m=0 to 2n+1, x=1-4, y=1-4, z=1-4 and with the proviso that x+y is ≦5. For the purposes of the present invention, y stands for the number of Cl anions present in the anion. The number z stands for the degree of charging of the cation and thus for the number of anions present in the compounds according to the invention. Overall, the electroneutrality of the compounds should be ensured.

The compounds according to the invention are preferably those of the formula (I) where m=0 and y=1. These preferred compounds are represented by the general formula (Ia):

$$[Kt]^{z+}{}_z[(C_nF_{2n+1})_xPClF_{5-x}]^- \qquad (Ia)$$

Particularly preferably, x=3 and/or n=2, 3 or 4. For the purposes of the present invention, the compounds are very particularly preferably selected from the group comprising $[Kt]^{z+}{}_z[(C_2F_5)_3PClF_2]^-$, $[Kt]^{z+}{}_z[(C_3F_7)_3PClF_2]^-$ or $[Kt]^{z+}{}_z[(C_4F_9)_3PClF_2]^-$.

There are no restrictions per se regarding the choice of cation of the compound (I) in accordance with the present invention. Thus, $[Kt]^{z+}$ can be an inorganic or organic cation. The cations are preferably organic cations and particularly preferably the organic cations selected from the group comprising ammonium, phosphonium, uronium, thiouronium, guanidinium cations or heterocyclic cations. Examples of organic cations are also polyammonium ions having a degree of charging z=4.

Ammonium cations can be described, for example, by the formula (1)

$$[NR_4]^+ \qquad (1),$$

where
R in each case, independently of one another, denotes
H,
OR', NR'$_2$, with the proviso that a maximum of one substituent R in formula (1) is OR', NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, where one or more R may be partially or fully substituted by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in R which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R' may be =H, non-, partially or perfluorinated C$_1$- to C$_{18}$-alkyl, C$_3$- to C$_7$-cycloalkyl, unsubstituted or substituted phenyl and X may be =halogen.

Phosphonium cations can be described, for example, by the formula (2)

$$[PR^2{}_4]^+ \qquad (2),$$

where
R$^2$ in each case, independently of one another, denotes
H, OR' or NR'$_2$,
straight-chain or branched alkyl having 1-20 C atoms,
straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more $R^2$ may be partially or fully substituted by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in $R^2$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated $C_1$- to $C_{18}$-alkyl, $C_3$- to $C_7$-cycloalkyl, unsubstituted or substituted phenyl and X=halogen.

However, cations of the formulae (1) and (2) in which all four or three substituents R and $R^2$ are fully substituted by halogens are excluded, for example the tris(trifluoromethyl)methylammonium cation, the tetra(trifluoromethyl)ammonium cation or the tetra(nonafluorobutyl)ammonium cation.

Uronium cations can be described, for example, by the formula (3)

[C(R$^3$R$^4$N)(OR$^5$)(NR$^6$R$^7$)]$^+$ (3), and thiouronium cations by the formula (4)

[(R$^3$R$^4$N)(SR$^5$)(NR$^6$R$^7$)]$^+$ (4), where $R^3$ to $R^7$ each, independently of one another, denote H, where H is excluded for $R^5$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents $R^3$ to $R^7$ may be partially or fully substituted by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in $R^3$ to $R^7$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated $C_1$- to $C_{18}$-alkyl, $C_3$- to $C_7$-cycloalkyl, unsubstituted or substituted phenyl and X=halogen.

Guanidinium cations can be described by the formula (5)

[C(NR$^8$R$^9$)(NR$^{10}$R$^{11}$)(NR$^{12}$R$^{13}$)]$^+$ (5), where $R^8$ to $R^{13}$ each, independently of one another, denote

H, —CN, NR'$_2$, —OR', straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents $R^8$ to $R^{13}$ may be partially or fully substituted by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in $R^8$ to $R^{13}$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated $C_1$- to $C_{18}$-alkyl, $C_3$- to $C_7$-cycloalkyl, unsubstituted or substituted phenyl and X=halogen.

In addition, it is possible to employ cations of the general formula (6)

[HetN]$^{z+}$ (6)

where

HetN$^{z+}$ denotes a heterocyclic cation selected from the group

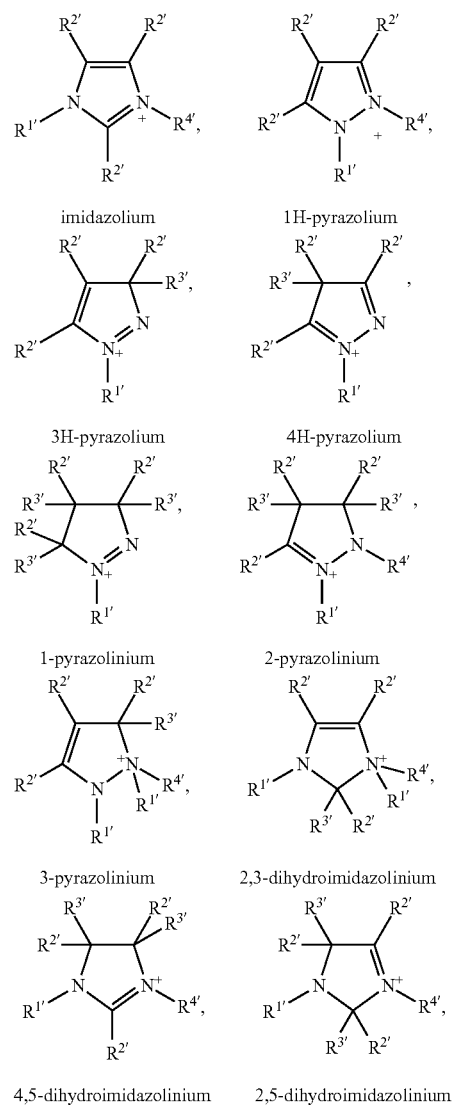

-continued pyrrolidinium
1,2,4-triazolium
1,2,4-triazolium
1,2,3-triazolium
1,2,3-triazolium
pyridinium
pyridazinium
pyrimidinium
piperidinium
morpholinium
piperazinium
piperazinium
pyrazinium
thiazolium
oxazolium -continued indolium
quinolinium
isoquinolinium
quinoxalinium
indolinium where the substituents
$R^{1'}$ to $R^{4'}$ each, independently of one another, denote
H,
F, Cl, Br, I, —CN, —OR', —NR'$_2$, —P(O)R'$_2$, —P(O)(OR')$_2$, —P(O)(NR'$_2$)$_2$, —C(O)R', —C(O)OR', —C(O)X, —C(O)NR'$_2$, —SO$_2$NR'$_2$, —SO$_2$OH, —SO$_2$X, —SR', —S(O)R', —SO$_2$R' and/or NO$_2$, with the proviso that $R^{1'}$, $R^{3'}$, $R^{4'}$ are H and/or a straight-chain or branched alkyl having 1-20 C atoms, straight-chain or branched alkenyl having 2-20 C atoms and one or more double bonds, straight-chain or branched alkyl having 1-20 C atoms,
straight-chain or branched alkenyl having 2-20 C atoms and one or more double bonds,
straight-chain or branched alkynyl having 2-20 C atoms and one or more triple bonds,
saturated, partially or fully unsaturated cycloalkyl having 3-7 C atoms, which may be substituted by alkyl groups having 1-6 C atoms, saturated, partially or fully unsaturated heteroaryl, heteroaryl-$C_1$-$C_6$-alkyl or aryl-$C_1$-$C_6$-alkyl, where the substituents $R^{1'}$, $R^{2'}$, $R^{3'}$ and/or $R^{4'}$ together may also form a ring system, where one or more substituents $R^{1'}$ to $R^{4'}$ may be partially or fully substituted by halogens, in particular —F and/or —Cl, or —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$, but where $R^{1'}$ and $R^{4'}$ cannot simultaneously be fully substituted by halogens and where, in the substituents $R^{1'}$ to $R^{4'}$, one or two non-adjacent carbon atoms which are not bonded to the heteroatom may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated $C_1$- to $C_{18}$-alkyl, $C_3$- to $C_7$-cycloalkyl, unsubstituted or substituted phenyl and X=halogen.

For the purposes of the present invention, fully unsaturated substituents are also taken to mean aromatic substituents.

In accordance with the invention, suitable substituents R and $R^2$ to $R^{13}$ of the compounds of the formulae (1) to (5), besides H, are preferably: $C_1$- to $C_{20}$-, in particular $C_1$- to $C_{14}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents R and $R^2$ in the compounds of the formula (1) or (2) may be identical or different. The substituents R and $R^2$ are preferably different.

The substituents R and $R^2$ are particularly preferably methyl, ethyl, isopropyl, propyl, butyl, sec-butyl, pentyl, hexyl, octyl, decyl or tetradecyl.

Up to four substituents of the guanidinium cation [C(NR$^8$R$^9$)(NR$^{10}$R$^{11}$)(NR$^{12}$R$^{13}$)]$^+$ may also be bonded in pairs in such a way that mono-, bi- or polycyclic cations are formed.

Without restricting generality, examples of such guanidinium cations are:

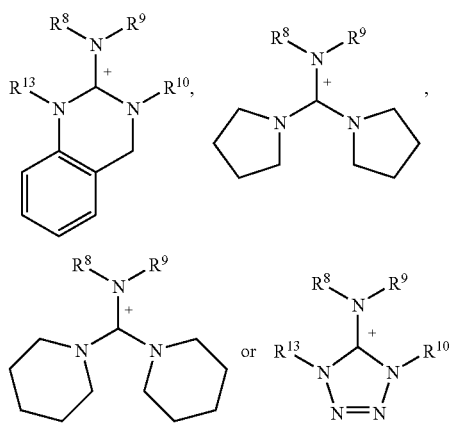

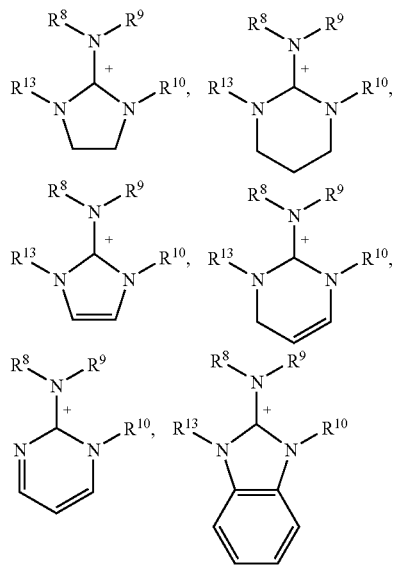

where the substituents $R^8$ to $R^{10}$ and $R^{13}$ can have a meaning or particularly preferred meaning indicated above.

If desired, the carbocycles or heterocycles of the guanidinium cations indicated above may also be substituted by $C_1$- to $C_6$-alkyl, $C_1$- to $C_6$-alkenyl, —CN, —NO$_2$, F, Cl, Br, I, —OH, —$C_1$-$C_6$-alkoxy, —NR'$_2$, —SR', —S(O)R', —SO$_2$R', —COOH, —SO$_2$NR'$_2$, —SO$_2$X' or —SO$_3$H, where X and R' have a meaning indicated above, substituted or unsubstituted phenyl or an un-substituted or substituted heterocycle.

Up to four substituents of the uronium cation [C(R$^3$R$^4$N)(OR$^5$)(NR$^6$R$^7$)]$^+$ or thiouronium cation [C(R$^3$R$^4$N)(SR$^5$)(NR$^6$R$^7$)]$^+$ may also be bonded in pairs in such a way that mono-, bi- or polycyclic cations are formed.

Without restricting generality, examples of such cations are indicated below, where Y=O or S:

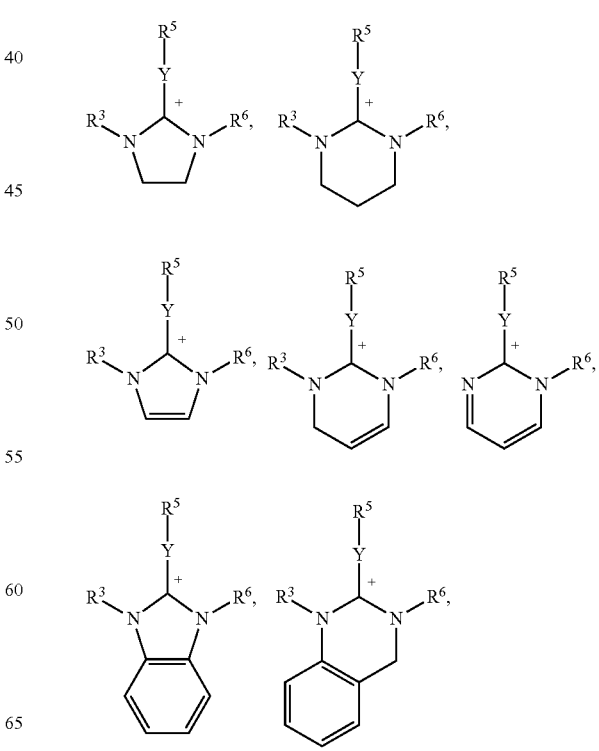

-continued

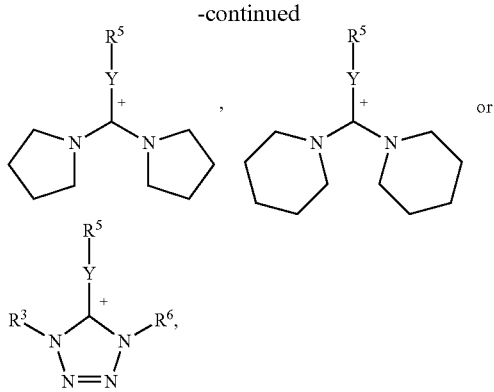

where the substituents $R^3$, $R^5$ and $R^6$ can have a meaning or particularly preferred meaning indicated above.

If desired, the carbocycles or heterocycles of the cations indicated above may also be substituted by $C_1$- to $C_6$-alkyl, $C_1$- to $C_6$-alkenyl, —CN, —NO$_2$, F, Cl, Br, I, —OH, —$C_1$-$C_6$-alkoxy, —NR'$_2$, —SR', —S(O)R', —SO$_2$R', —COOH, SO$_2$NR'$_2$, SO$_2$X or SO$_3$H or substituted or unsubstituted phenyl or an un-substituted or substituted heterocycle, where X and R' have a meaning indicated above.

The substituents $R^3$ to $R^{13}$ are each, independently of one another, preferably a straight-chain or branched alkyl group having 1 to 16 C atoms. The substituents $R^3$ and $R^4$, $R^6$ and $R^7$, $R^8$ and $R^9$, $R^{10}$ and $R^{11}$ and $R^{12}$ and $R^{13}$ in compounds of the formulae (3) to (5) may be identical or different. $R^3$ to $R^{13}$ are particularly preferably each, independently of one another, methyl, ethyl, n-propyl, isopropyl, n-butyl, tert-butyl, sec-butyl, phenyl, hexyl or cyclohexyl, very particularly preferably methyl, ethyl, n-propyl, isopropyl, n-butyl or hexyl.

In accordance with the invention, suitable substituents $R^{1'}$ to $R^{4'}$ of compounds of the formula (6), besides H, are preferably: $C_1$- to $C_{20}$-, in particular $C_1$- to $C_{12}$-alkyl groups, and saturated or unsaturated, i.e. also aromatic, $C_3$- to $C_7$-cycloalkyl groups, which may be substituted by $C_1$- to $C_6$-alkyl groups, in particular phenyl.

The substituents $R^{1'}$ and $R^{4'}$ are each, independently of one another, particularly preferably methyl, ethyl, isopropyl, propyl, butyl, sec-butyl, tert-butyl, pentyl, hexyl, octyl, decyl, cyclohexyl, phenyl or benzyl. They are very particularly preferably methyl, ethyl, n-butyl or hexyl. In pyrrolidinium, piperidinium or indolinium compounds, the two substituents $R^{1'}$ and $R^{4'}$ are preferably different.

The substituent $R^{2'}$ or $R^{3'}$ is in each case, independently of one another, in particular H, methyl, ethyl, isopropyl, propyl, butyl, sec-butyl, tert-butyl, cyclohexyl, phenyl or benzyl. $R^{2'}$ is particularly preferably H, methyl, ethyl, isopropyl, propyl, butyl or sec-butyl. $R^{2'}$ and $R^{3'}$ are very particularly preferably H.

The $C_1$-$C_{12}$-alkyl group is, for example, methyl, ethyl, isopropyl, propyl, butyl, sec-butyl or tert-butyl, furthermore also pentyl, 1-, 2- or 3-methylbutyl, 1,1-, 1,2- or 2,2-dimethylpropyl, 1-ethylpropyl, hexyl, heptyl, octyl, nonyl, decyl, undecyl or dodecyl. Optionally difluoromethyl, trifluoromethyl, pentafluoroethyl, heptafluoropropyl or nonafluorobutyl.

A straight-chain or branched alkenyl having 2 to 20 C atoms, in which a plurality of double bonds may also be present, is, for example, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{20}H_{39}$, preferably allyl, 2- or 3-butenyl, isobutenyl, sec-butenyl, furthermore preferably 4-pentenyl, isopentenyl or hexenyl.

A straight-chain or branched alkynyl having 2 to 20 C atoms, in which a plurality of triple bonds may also be present, is, for example, ethynyl, 1- or 2-propynyl, 2- or 3-butynyl, furthermore 4-pentynyl, 3-pentynyl, hexynyl, heptynyl, octynyl, —$C_9H_{15}$, —$C_{10}H_{17}$ to —$C_{20}H_{37}$, preferably ethynyl, 1- or 2-propynyl, 2- or 3-butynyl, 4-pentynyl, 3-pentynyl or hexynyl.

Aryl-$C_1$-$C_6$-alkyl denotes, for example, benzyl, phenylethyl, phenylpropyl, phenylbutyl, phenylpentyl or phenylhexyl, where both the phenyl ring and also the alkylene chain may be partially or fully substituted, as described above, by halogens, in particular —F and/or —Cl, or partially by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$.

Unsubstituted saturated or partially or fully unsaturated cycloalkyl groups having 3-7 C atoms are therefore cyclopropyl, cyclobutyl, cyclopentyl, cyclohexyl, cycloheptyl, cyclopentenyl, cyclopenta-1,3-dienyl, cyclohexenyl, cyclohexa-1,3-dienyl, cyclohexa-1,4-dienyl, phenyl, cycloheptenyl, cyclohepta-1,3-dienyl, cyclohepta-1,4-dienyl or cyclohepta-1,5-dienyl, each of which may be substituted by $C_1$- to $C_6$-alkyl groups, where the cycloalkyl group or the cycloalkyl group substituted by $C_1$- to $C_6$-alkyl groups may in turn also be substituted by halogen atoms, such as F, Cl, Br or I, in particular F or Cl, or by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$.

In the substituents R, $R^2$ to $R^{13}$ or $R^{1'}$ to $R^{4'}$, one or two non-adjacent carbon atoms which are not bonded in the α-position to the heteroatom may also be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—, where R'=non-, partially or perfluorinated $C_1$- to $C_{18}$-alkyl, $C_3$- to $C_7$-cycloalkyl, unsubstituted or substituted phenyl.

Without restricting generality, examples of substituents R, $R^2$ to $R^{13}$ and $R^{1'}$ to $R^{4'}$ modified in this way are: —OCH$_3$, —OCH(CH$_3$)$_2$, —CH$_2$OCH$_3$, —CH$_2$—CH$_2$—O—CH$_3$, —C$_2$H$_4$OCH(CH$_3$)$_2$, —C$_2$H$_4$SC$_2$H$_5$, —C$_2$H$_4$SCH(CH$_3$)$_2$, —S(O)CH$_3$, —SO$_2$CH$_3$, —SO$_2$C$_6$H$_5$, —SO$_2$C$_3$H$_7$, —SO$_2$CH(CH$_3$)$_2$, —SO$_2$CH$_2$CF$_3$, —CH$_2$SO$_2$CH$_3$, —O—C$_4$H$_8$—O—C$_4$H$_9$, —CF$_3$, —C$_2$F$_5$, —C$_3$F$_7$, —C$_4$F$_9$, —C(CF$_3$)$_3$, —CF$_3$SO$_2$CF$_3$, —C$_2$F$_4$N(C$_2$F$_5$)C$_2$F$_5$, —CHF$_2$, —CH$_2$CF$_3$, —C$_2$F$_2$H$_3$, —C$_3$H$_6$, —CH$_2$C$_3$F$_7$, —C(CFH$_2$)$_3$, —CH$_2$C(O)OH, —CH$_2$C$_6$H$_5$, —C(O)C$_6$H$_5$ or P(O)(C$_2$H$_5$)$_2$.

In R', $C_3$- to $C_7$-cycloalkyl is, for example, cyclopropyl, cyclobutyl, cyclopentyl, cyclohexyl or cycloheptyl.

In R', substituted phenyl denotes phenyl which is substituted by $C_1$- to $C_6$-alkyl, $C_1$- to $C_6$-alkenyl, —CN, —NO$_2$, F, Cl, Br, I, —OH, —$C_1$-$C_6$-alkoxy, NR'$_2$, —COOH, —SO$_2$X', —SR", —S(O)R", —SO$_2$R", SO$_2$NR'$_2$ or SO$_3$H, where X' denotes F, Cl or Br and R" denotes a non-, partially or perfluorinated $C_1$- to $C_6$-alkyl or $C_3$- to $C_7$-cycloalkyl as defined for R', for example o-, m- or p-methylphenyl, o-, m- or p-ethylphenyl, o-, m- or p-propylphenyl, o-, m- or p-isopropylphenyl, o-, m- or p-tert-butylphenyl, o-, m- or p-nitrophenyl, o-, m- or p-hydroxyphenyl, o-, m- or p-methoxyphenyl, o-, m- or p-ethoxyphenyl, o-, m-, p-(trifluoromethyl)phenyl, o-, m-, p-(trifluoromethoxy)phenyl, o-, m-, p-(trifluoromethylsulfonyl)phenyl, o-, m- or p-fluorophenyl, o-, m- or p-chlorophenyl, o-, m- or p-bromophenyl, o-, m- or p-iodophenyl, further preferably 2,3-, 2,4-, 2,5-, 2,6-, 3,4- or 3,5-dimethylphenyl, 2,3-, 2,4-, 2,5-, 2,6-, 3,4- or 3,5-dihydroxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl, 5-fluoro-2-methylphenyl, 3,4,5-trimethoxyphenyl or 2,4,5-trimethylphenyl.

In $R^{1'}$ to $R^{4'}$, heteroaryl is taken to mean a saturated or unsaturated mono- or bicyclic heterocyclic radical having 5 to 13 ring members, in which 1, 2 or 3 N and/or 1 or 2 S or O atoms may be present and the heterocyclic radical may be mono- or polysubstituted by $C_1$- to $C_6$-alkyl, $C_1$- to $C_6$-alkenyl, —CN, —NO$_2$, F, Cl, Br, I, —OH, —NR'$_2$, —C$_1$-C$_6$-alkoxy, —COOH, —SO$_2$X', —SO$_2$NR'$_2$, —SR", —S(O)R", —SO$_2$R" or SO$_3$H, where X' and R" have a meaning indicated above.

The heterocyclic radical is preferably substituted or unsubstituted 2- or 3-furyl, 2- or 3-thienyl, 1-, 2- or 3-pyrrolyl, 1-, 2-, 4- or 5-imidazolyl, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl or 1-, 2- or 3-pyrrolidinyl.

Heteroaryl-$C_1$-$C_6$-alkyl is, analogously to aryl-$C_1$-$C_6$-alkyl, taken to mean, for example, pyridinylmethyl, pyridinylethyl, pyridinylpropyl, pyridinylbutyl, pyridinylpentyl, pyridinylhexyl, where the heterocycles described above may furthermore be linked to the alkylene chain in this way.

HetN$^{z+}$ is preferably

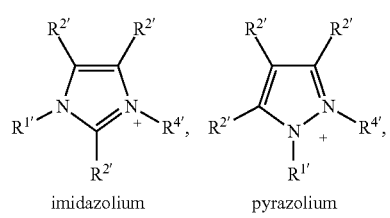

imidazolium    pyrazolium

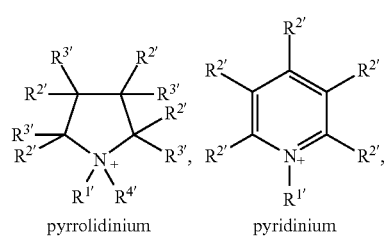

pyrrolidinium    pyridinium

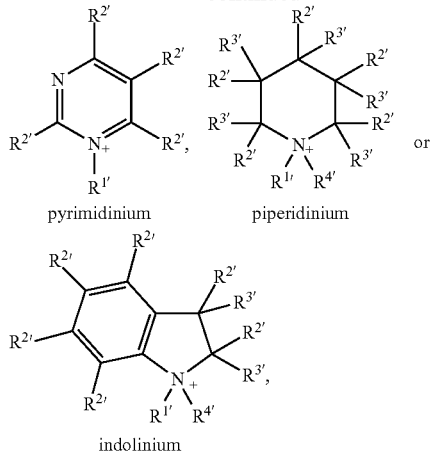

pyrimidinium    piperidinium indolinium where the substituents $R^{1'}$ to $R^{4'}$ each, independently of one another, have a meaning described above.

In a further embodiment of the present invention, the cation $[Kt]^{z+}$ can be a $[(R°)_3O]^+$ cation or an $[(R°)_3S]^+$ cation, where R° denotes straight-chain or branched alkyl groups having 1-8 C atoms or unsubstituted phenyl or phenyl which is substituted by R°, OR°, N(R°)$_2$, CN or halogen.

R° of the $[(R°)_3O]^+$ cation or $[(R°)_3S]^+$ cation is preferably straight-chain alkyl having 1-8 C atoms, preferably having 1-4 C atoms, in particular methyl or ethyl, very particularly preferably ethyl.

The cation $[Kt]^{z+}$ may in addition also be inorganic, in particular a metal cation. The metal cation may comprise metals from groups 1 to 12 of the Periodic Table, in particular alkali metals. The metal is preferably selected from the group comprising Li, K, Rb, Cs.

The cations of the compounds according to the invention are preferably ammonium, phosphonium, guanidinium or heterocyclic cations, particularly preferably heterocyclic cations (HetN$^{z+}$). HetN$^{z+}$ is particularly preferably imidazolium, pyrrolidinium or pyridinium, as defined above, where the substituents $R^{1'}$ to $R^{4'}$ each, independently of one another, have a meaning described above. HetN$^{z+}$ is very particularly preferably imidazolium, where the substituents $R^{1'}$ to $R^{4'}$ each, independently of one another, have a meaning described above. The compounds of the formula (1) are very particularly preferably imidazolium, pyrrolidinium, pyridinium, ammonium, phosphonium, guanidinium salts containing $[(C_2F_5)_3PClF_2]^-$, $[(C_3F_7)_3PClF_2]^-$ or $[(C_4F_9)_3PClF_2]^-$ anions.

It goes without saying to the person skilled in the art that substituents, such as, for example, C, H, N, O, Cl, F, in the compounds according to the invention may be replaced by the corresponding isotopes.

The present invention likewise relates to processes for the preparation of compounds containing organofluorochlorophosphate anions comprising the reaction of a chloride salt with organofluorophosphoranes.

The processes according to the invention are preferably those for the preparation of a compound of the formula (I), as described above, comprising the reaction of $[Kt]^{z+}z[Cl]^-$ with a compound of the general formula (II)

$$(C_nH_mF_{2n+1-m})_xPF_{5-x} \quad (II)$$

in which $[Kt]^{z+}$ denotes an inorganic or organic cation where z=1-4, and in compounds of the formula II n=1-12, m=0 to 2n+1, x=1-4 and y=1-4. Preferably, y=1 and m=0, i.e. $[Kt]^{30}$ Cl$^-$ is preferably reacted with a compound of the general formula (IIa)

(IIa)

in which [Kt]$^+$ denotes an inorganic or organic cation, and in formula IIa n=1-12 and x=1-4.

The preparation of perfluoroalkylphosphoranes (formula (II) or (IIa)) as starting compounds for the process according to the invention is familiar to the person skilled in the art from the prior art, for example from the German Patent Application DE 19 846 636 A1, which is hereby incorporated by way of reference and is thus regarded as part of the disclosure.

The process according to the invention can be carried out at temperatures of −40 to 180° C., preferably at 0 to 50° C. and very particularly preferably at room temperature.

The reaction is carried out, in particular, in a solvent, but can also be carried out in the absence of a solvent.

Suitable solvents are those selected from the group of the nitriles, dialkyl carbonates, glymes, dialkyl ethers, cyclic ethers, dimethylformamide, dimethyl sulfoxide, dichloromethane, water or mixtures thereof. Preferred examples of suitable solvents are acetonitrile and glymes.

The reaction duration is usually 5 minutes to 24 hours, preferably 1 hour to 10 hours.

When the reaction is complete, the compounds according to the invention can be worked up and purified in a manner known to the person skilled in the art, for example by removal of volatile constituents in vacuo and drying, where further purification steps can follow if necessary.

Many of the said compounds according to the invention are suitable for use as ionic liquid or are preferably ionic liquids and can thus be used in a whole series of application systems.

The present invention furthermore relates to the use of the compounds according to the invention as solvent or solvent additive, as phase-transfer catalyst, as extractant, as heat-transfer medium, as surface-active substance, as plasticiser, as flameproofing agent, as additive or as conductive salt and catalysts in chemical processes.

In the case of the use of the said compounds as solvent, these are suitable in any type of reaction known to the person skilled in the art, for example for transition metal- or enzyme-catalysed reactions, such as, for example, hydroformylation reactions, Friedel-Crafts reactions, oligomerisation reactions, esterifications or isomerisation reactions, where the said list is not definitive.

In the case of use as extractant, the compounds can be employed for separating off reaction products, but also for separating off impurities, depending on the solubility of the respective component in the compound according to the invention used. In addition, the compounds of the formula (I) can also serve as separating agents in the separation of a plurality of components, for example in the separation of a plurality of components of a mixture by distillation.

Further potential applications are the use as plasticiser in polymer materials, as flameproofing agent for a series of materials or applications and as conductive salt in different electrochemical cells and applications, for example in galvanic cells, in capacitors or in fuel cells.

The present invention likewise relates to electrolytes, electrochemical cells, capacitors or fuel cells comprising at least one compound of the general formula (I) according to the invention. The compounds according to the invention can be used in the said applications in combination with all materials and additives known to the person skilled in the art without requiring an inventive step by the person skilled in the art.

In addition, the compounds according to the invention are suitable for the preparation of organophosphinates. In the case of water as solvent, the organofluorochlorophosphates initially formed can react further with water, with formation of corresponding organophosphinates. Alternatively, the organophosphinates can also be prepared by dissolving the organofluorochlorophosphates prepared in accordance with the invention in water. The organofluorochlorophosphates according to the invention are accordingly suitable for use for the preparation of organophosphinates. These organophosphinates are themselves again valuable compounds which can be employed, for example, as ionic liquids. Corresponding organophosphinates are disclosed, for example, in WO 2003/087110, the disclosure content of which is hereby incorporated by way of reference.

Processes according to the invention for the preparation of organophosphinates comprise the reaction of a compound in accordance with the present invention with water or water-containing solvents or solvent mixtures. This reaction can be carried out at temperatures of −40 to 200° C., at atmospheric pressure up to pressures of 100 bar. The reaction is preferably carried out with water at room temperature and atmospheric pressure.

Even without further comments, it is assumed that a person skilled in the art will be able to utilise the above description in the broadest scope. The preferred embodiments and examples should therefore merely be regarded as descriptive disclosure which is absolutely not limiting in any way.

The $^1$H-, $^{19}$F- and $^{31}$P-NMR spectra are measured in a Bruker ARX 400 spectrometer (400.13 MHz for $^1$H, 376.46 for $^{19}$F and 161.98 for $^{31}$P) in acetonitrile-$D_3$, unless indicated otherwise in the examples. CCl$_3$F and TMS are employed as internal reference in the measurement of the $^{19}$F NMR and proton NMR spectra. For the $^{31}$P NMR spectra, 85% H$_3$PO$_4$ in D$_2$O in acetonitrile-$D_3$ is measured as external reference in a separate experiment at a frequency of 230.11 Hz.

EXAMPLES

Example 1

Tetrabutylammonium tris(pentafluoroethyl)difluorochlorophosphate

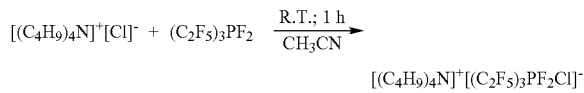

A mixture of 7.04 g (25.3 mmol) of tetrabutylammonium chloride and 12.0 g (28.2 mmol) of tris(pentafluoroethyl)difluorophosphorane is dissolved in 20 ml of acetonitrile, and the mixture is stirred at room temperature for one hour. Volatile constituents (excesses of tris(pentafluoroethyl)difluorophosphorane and acetonitrile) are removed in vacuo, and the residue is dried in vacuo for two hours at 7 Pa and at 40-50° C. (temperature of the oil bath). 17.0 g of a viscous, oily material are obtained. The yield of tetrabutylammonium tris(pentafluoroethyl)difluoro-chlorophosphate is 95.5%, based on the tetrabutylammonium chloride employed. The compound is analysed by NMR spectroscopy.

NMR data:

$^1$H NMR spectrum, ppm: 0.96 t (CH$_3$), 1.35 t, q (CH$_2$), 1.59 m (CH$_2$), 3.06 m (CH$_2$); $J^3_{H,H}$=7.4 Hz.

$^{19}$F NMR spectrum, ppm: −25.52 d, m (PF), −69.83 d, m (PF), −77.49 t (CF$_3$), −80.04 m (2CF$_3$), −105.12 d, d (CF$_2$, F$_A$), −105.87 d, d (CF$_2$, F$_B$), −108.89 d, m (CF$_2$), −114.72 d, m (CF$_2$, F$_A$), −115.45 d, m (CF$_2$, F$_B$), J$^1_{P,F}$=933 Hz, J$^1_{P,F}$=863 Hz, J$^2_{P,F}$=98 Hz, J$^2_{P,F}$=82 Hz, J$^2_{P,F}$=116 Hz, J$^2_{A,B}$=281 Hz, J$^4_{F,F}$=21 Hz.
$^{31}$P NMR spectrum, ppm: −147.4 d, d, m.

Example 2

Benzyltriethylammonium tris(pentafluoroethyl)difluorochlorophosphate

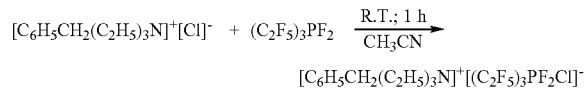

A mixture of 11.45 g (50.3 mmol) of benzyltriethylammonium chloride and 23.6 g (55.4 mmol) of tris(pentafluoroethyl)difluorophosphorane is dissolved in 30 ml of acetonitrile, and the mixture is stirred at room temperature for one hour. Volatile constituents (excesses of tris(pentafluoroethyl)difluorophosphorane and acetonitrile) are removed in vacuo, and the residue is dried in vacuo for two hours at 7 Pa and at 40-50° C. (temperature of the oil bath). 32.3 g of a viscous, oily material are obtained. The yield of benzyltriethylammonium tris(pentafluoroethyl)difluorochlorophosphate is 98.2%, based on the benzyltriethylammonium chloride employed. The compound is analysed by NMR spectroscopy.

NMR data:
$^1$H NMR spectrum, ppm: 1.34 t, t (3CH$_3$), 3.14 q (3CH$_2$), 4.30 S(CH$_2$), 7.44-7.58 m (C$_6$H$_5$); J$^3_{H,H}$=7.3 Hz.
$^{19}$F NMR spectrum, ppm: −25.52 d, m (PF), −69.81 d, m (PF), −77.47 t (CF$_3$), −80.03 m (2CF$_3$), −105.11 d, d (CF$_2$, F$_A$), −105.85 d, d (CF$_2$, F$_B$), −108.87 d, m (CF$_2$), −114.72 d, m (CF$_2$, F$_A$), −115.45 d, m (CF$_2$, F$_B$), J$^1_{P,F}$=928 Hz, J$^1_{P,F}$=861 Hz, J$^2_{P,F}$=99 Hz, J$^2_{P,F}$=82 Hz, J$^2_{P,F}$=116 Hz, J$^2_{A,B}$=280 Hz, J$^4_{F,F}$=21 Hz.
$^{31}$P NMR spectrum, ppm: −147.4 d, d, m.

Example 3

1-Ethyl-3-methylimidazolium tris(pentafluoroethyl)difluorochlorophosphate

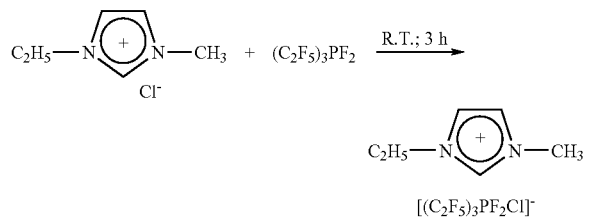

A mixture of 4.1 g (28.0 mmol) of 1-ethyl-3-methylimidazolium chloride and 13.1 g (30.8 mmol) of tris(pentafluoroethyl)difluorophosphorane is stirred at room temperature for three hours. Volatile constituents (excesses of tris(pentafluoroethyl)difluorophosphorane) are removed in vacuo, and the residue is dried in vacuo for two hours at 7 Pa and at 40-50° C. (temperature of the oil bath). 15.9 g of a viscous, oily material are obtained. The yield of 1-ethyl-3-methylimidazolium tris(pentafluoroethyl)difluorochlorophosphate is 99.2%, based on the 1-ethyl-3-methylimidazolium chloride employed. The compound is analysed by NMR spectroscopy.

NMR data:
$^1$H NMR spectrum, ppm: 1.45 t (CH$_3$); 3.83 s (CH$_3$); 4.17 q (CH$_2$); 7.37 m (CH); 7.43 m (CH); 8.57 br. s. (CH); $^3$J$_{H,H}$=7.3 Hz.
$^{19}$F NMR spectrum, ppm: −25.52 d, m (PF), −69.83 d, m (PF), −77.48 t (CF$_3$), −80.04 m (2CF$_3$), −105.12 d, d (CF$_2$, F$_A$), −105.87 d, d (CF$_2$, F$_B$), −108.87 d, m (CF$_2$), −114.72 d, m (CF$_2$, F$_A$), −115.47 d, m (CF$_2$, F$_B$), J$^1_{P,F}$=933 Hz, J$^1_{P,F}$=863 Hz, J$^2_{P,F}$=98 Hz, J$^2_{P,F}$=84 Hz, J$^2_{P,F}$=119 Hz, J$^2_{A,B}$=281 Hz, J$^4_{F,F}$=21 Hz.
$^{31}$P NMR spectrum, ppm: −147.4 d, d, m.

Example 4

1-Butyl-1-methylpyrrolidinium tris(pentafluoroethyl)difluorochlorophosphate

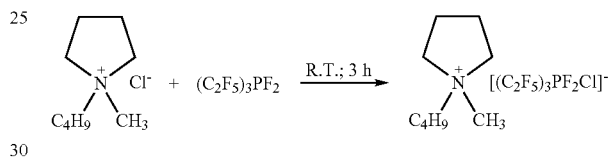

A mixture of 4.03 g (22.7 mmol) of 1-butyl-1-methylpyrrolidinium chloride and 10.8 g (25.4 mmol) of tris(pentafluoroethyl)difluorophosphorane is stirred at room temperature for three hours. Volatile constituents (excesses of tris(pentafluoroethyl)difluorophosphorane) are removed in vacuo, and the residue is dried in vacuo for two hours at 7 Pa and at 40-50° C. (temperature of the oil bath). 13.6 g of a viscous, oily material are obtained. The yield of 1-butyl-1-methylpyrrolidinium tris(pentafluoroethyl)difluorochlorophosphate is 99.2%, based on the 1-butyl-1-methylpyrrolidinium chloride employed. The compound is analysed by NMR spectroscopy.

NMR data:
$^1$H NMR spectrum, ppm: 0.96 t (CH$_3$), 1.36 t, q (CH$_2$), 1.69 m (CH$_2$), 2.14 m (2CH$_2$), 2.93 S(CH$_3$), 3.21 m (CH$_2$), 3.39 m (2CH$_2$); J$^3_{H,H}$=7.4 Hz.
$^{19}$F NMR spectrum, ppm: −25.52 d, m (PF), −69.81 d, m (PF), −77.48 t (CF$_3$), −80.03 m (2CF$_3$), −105.13 d, d (CF$_2$, F$_A$), −105.87 d, d (CF$_2$, F$_B$), −108.89 d, m (CF$_2$), −114.72 d, m (CF$_2$, F$_A$), −115.45 d, m (CF$_2$, F$_B$), J$^1_{P,F}$=931 Hz, J$^1_{P,F}$=861 Hz, J$^2_{P,F}$=98 Hz, J$^2_{P,F}$=82 Hz, J$^2_{P,F}$=116 Hz, J$^2_{A,B}$=281 Hz, J$^4_{F,F}$=21 Hz.
$^{31}$P NMR spectrum, ppm: −147.4 d, d, m.

Example 5

Trihexyltetradecylphosphonium tris(pentafluoroethyl)difluorochlorophosphate

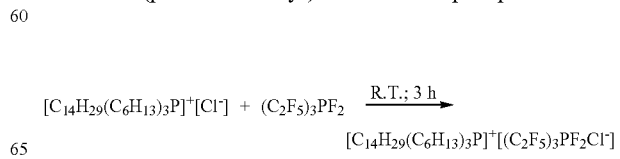

A mixture of 6.57 g (12.7 mmol) of trihexyltetradecylphosphonium chloride and 5.92 g (13.9 mmol) of tris(pentafluoroethyl)difluorophosphorane is stirred at room temperature for three hours. Volatile constituents (excesses of tris(pentafluoroethyl)difluorophosphorane) are removed in vacuo, and the residue is dried in vacuo for two hours at 7 Pa and at 40-50° C. (temperature of the oil bath). 11.96 g of a viscous, oily material are obtained. The yield of trihexyltetradecylphosphonium tris(pentafluoroethyl)difluorochlorophosphate is 99.6%, based on the trihexyltetradecylphosphonium chloride employed. The compound is analysed by NMR spectroscopy.

NMR data:

$^1$H NMR spectrum, ppm: 0.90 m (4CH$_3$), 1.28 m (8CH$_2$), 1.31 m (8CH$_2$), 1.37-1.55 m (8CH$_2$), 1.97-2.07 m (4CH$_2$).

$^{19}$F NMR spectrum, ppm: −25.53 d, m (PF), −69.85 d, m (PF), −77.50 t (CF$_3$), −80.06 m (2CF$_3$), −105.15 d, d (CF$_2$, F$_A$), −105.89 d, d (CF$_2$, F$_B$), −108.91 d, m (CF$_2$), −114.76 d, m (CF$_2$, F$_A$), −115.49 d, m (CF$_2$, F$_B$), $J^1_{P,F}$=931 Hz, $J^1_{P,F}$=861 Hz, $J^2_{P,F}$=98 Hz, $J^2_{P,F}$=84 Hz, $J^2_{P,F}$=123 Hz, $J^2_{A,B}$=280 Hz, $J^4_{F,F}$=21 Hz.

$^{31}$P NMR spectrum, ppm: 33.4 (1P), −147.4 d, d, m (1P).

Example 6

Tetrakis(dimethylamino)ethylidenium di[tris(pentafluoroethyl)difluorochlorophosphate]

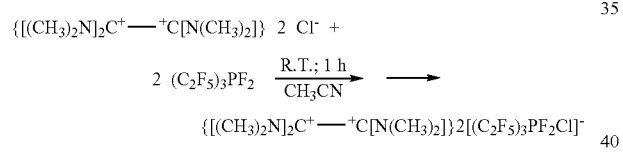

A mixture of 1.6 g (5.9 mmol) of tetrakis(dimethylamino)ethylidenium dichloride and 5.6 g (13.1 mmol) of tris(pentafluoroethyl)difluorophosphorane is dissolved in 20 ml of acetonitrile, and the mixture is stirred at room temperature for one hour. Volatile constituents (excesses of tris(pentafluoroethyl)difluorophosphorane and acetonitrile) are removed in vacuo, and the residue is dried in vacuo for two hours at 7 Pa and at 40-50° C. (temperature of the oil bath). 6.6 g of a viscous, oily material are obtained. The yield of tetrakis(dimethylamino)ethylidenium di[tris(pentafluoroethyl)difluorochlorophosphate] is 99.7%, based on the tetrakis(dimethylamino)ethylidenium dichloride employed. The compound is analysed by NMR spectroscopy.

NMR data:

$^1$H NMR spectrum, ppm: 3.14 s (2CH$_3$), 3.43 s (2CH$_3$).

$^{19}$F NMR spectrum, ppm: −25.52 d, m (PF), −69.83 d, m (PF), −77.46 t (CF$_3$), −80.00 m (2CF$_3$), −105.07 d, d (CF$_2$, F$_A$), −105.82 d, d (CF$_2$, F$_B$), −108.85 d, m (CF$_2$), −114.68 d, m (CF$_2$, F$_A$), −115.45 d, m (CF$_2$, F$_B$), $J^1_{P,F}$=933 Hz, $J^1_{P,F}$=861 Hz, $J^2_{P,F}$=96 Hz, $J^2_{P,F}$=82 Hz, $J^2_{P,F}$=120 Hz, $J^2_{A,B}$=282 Hz, $J^4_{F,F}$=21 Hz.

$^{31}$P NMR spectrum, ppm: −147.3 d, d, m.

Example 7

1-Butyl-1-methylpyrrolidinium tris(heptafluoropropyl)difluorochlorophosphate

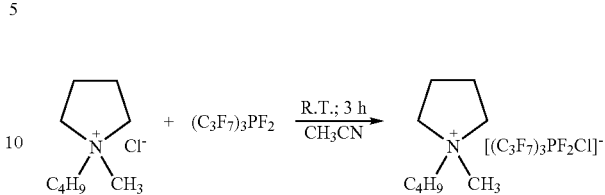

A mixture of 1.10 g (6.19 mmol) of 1-butyl-1-methylpyrrolidinium chloride and 3.57 g (6.19 mmol) of tris(heptafluoropropyl)difluorophosphorane is dissolved in 5 ml of acetonitrile, and the mixture is stirred at room temperature for three hours. Acetonitrile is removed in vacuo, and the residue is dried in vacuo for one hour at 7 Pa and room temperature. 4.31 g of a viscous, oily material are obtained. The yield of 1-butyl-1-methylpyrrolidinium tris(pentafluoroethyl)difluorochlorophosphate is 92.4%. The compound is analysed by NMR spectroscopy.

NMR data:

$^1$H NMR spectrum, ppm: 0.95 t (CH$_3$), 1.36 t, q (CH$_2$), 1.71 m (CH$_2$), 2.14 m (2CH$_2$), 2.93 s (CH$_3$), 3.22 m (CH$_2$), 3.40 m (2CH$_2$); $J^3_{H,H}$=7.4 Hz.

$^{19}$F NMR spectrum, ppm: −24.42 d, m (PF), −67.12 d, m (PF), −79.57 m (3CF$_3$), −102.35 d (CF$_2$, F$_A$), −103.12 d (CF$_2$, F$_B$), −105.71 d, m (CF$_2$), −111.98 d, m (CF$_2$, F$_A$), −112.76 d, m (CF$_2$, F$_B$), −120.98 t(CF$_2$), −124.11 m (CF$_2$), −124.29 m (CF$_2$), $J^1_{P,F}$=937 Hz, $J^1_{P,F}$=882 Hz, $J^2_{P,F}$=101 Hz, $J^2_{P,F}$=82 Hz, $J^2_{P,F}$=119 Hz, $J^2_{A,B}$=287 Hz.

$^{31}$P NMR spectrum, ppm: −139.3 d, d, m.

Example 8

Tetramethylammonium tris(pentafluoroethyl)difluorochlorophosphate

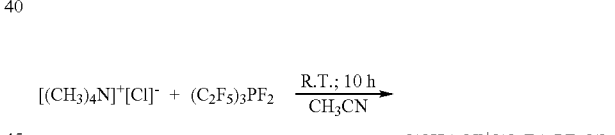

A mixture of 0.68 g (6.20 mmol) of tetramethylammonium chloride and 2.65 g (6.22 mmol) of tris(pentafluoroethyl)difluorophosphorane is dissolved in 5 ml of acetonitrile, and the mixture is stirred at room temperature for ten hours. Volatile constituents (excesses of tris(pentafluoroethyl)difluorophosphorane and acetonitrile) are removed in vacuo, and the residue is dried in vacuo for 0.5 hour at 7 Pa and room temperature. 3.26 g of a solid material are obtained. The yield of tetramethylammonium tris(pentafluoroethyl)difluorochlorophosphate is 98.2%, based on the tetramethylammonium chloride employed. The compound (three different isomers) is analysed by NMR spectroscopy.

NMR data:

$^1$H NMR spectrum, ppm: 3.07 s (4CH$_3$).

$^{19}$F NMR spectrum (facial isomer), ppm: −68.9 br. d (PF$_2$), −78.25 m (2CF$_3$), −78.85 m (CF$_3$), −106.2 br. m (CF$_2$), −112.4 m (2CF$_2$), $J^1_{P,F}$=960 Hz.

$^{19}$F NMR spectrum (meridional isomer 1), ppm: −22.44 d, m (PF$_2$), −78.2 m (2CF$_3$), −81.3 m (CF$_3$), −106.2 br. m (CF$_2$), −108.0 d, m (2CF$_2$), $J^1_{P,F}$=873 Hz, $J^2_{P,F}$=85 Hz.

$^{19}$F NMR spectrum (meridional isomer 2), ppm: −25.50 d, m (PF), −69.83 d, m (PF), −77.48 t (CF$_3$), −80.03 m (2CF$_3$), −105.12 d, d (CF$_2$, F$_A$), −105.87 d, d (CF$_2$, F$_B$), −108.87 d, m (CF$_2$), −114.69 d, m (CF$_2$, F$_A$), −115.42 d, m (CF$_2$, F$_B$), $J^1_{P,F}$=928 Hz, $J^1_{P,F}$=861 Hz, $J^2_{P,F}$=100 Hz, $J^2_{P,F}$=82 Hz, $J^2_{P,F}$=116 Hz, $J^2_{A,B}$=282 Hz, $J^4_{F,F}$=22 Hz.

$^{31}$P NMR spectrum, ppm: −137.0 t, m (facial isomer), −147.3 d, d, m (meridional isomer 2), −149.9 t, m (meridional isomer 1).

Example 9

1-Butyl-1-methylpyrrolidinium tris(pentafluoroethyl)difluorochlorophosphate

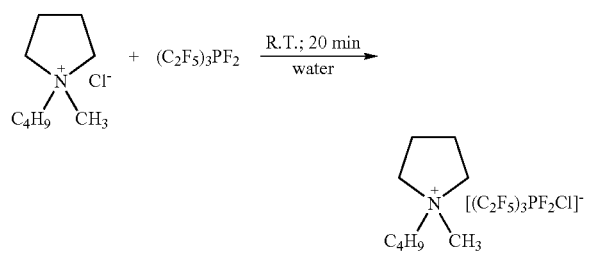

0.60 g (3.38 mmol) of 1-butyl-1-methylpyrrolidinium chloride is dissolved in 0.61 g of water at room temperature. 1.44 g (3.38 mmol) of tris(pentafluoroethyl)difluorophosphorane are added dropwise to this solution over the course of one minute at room temperature. The reaction mixture is stirred at room temperature for 20 min. A clear lower phase of the liquid product forms, 1-butyl-1-methylpyrrolidinium tris (pentafluoroethyl)difluorochlorophosphate, which is separated off (1.77 g) and analysed by spectroscopy.

NMR data:
$^{19}$F NMR spectrum (facial isomer), solvent-water, electronic standard (CCl$_3$F), ppm: −80.88 br. s (CF$_3$), −82.15 br. s (2CF$_3$), −87.09 br. d (PF$_2$), −114.71 br. d (3CF$_2$), $J^2_{P,F}$=87 Hz, $J^1_{P,F}$=845 Hz.

$^{31}$P NMR spectrum (facial isomer), solvent-water, electronic standard (H$_3$PO$_4$), ppm: −147.7 t, hep.

Example 10

1-Ethyl-3-methylimidazolium bis(pentafluoroethyl)phosphinate

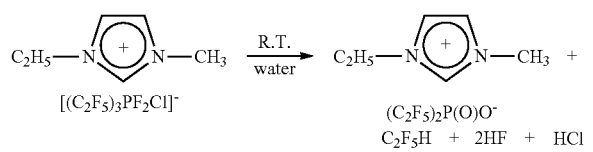

0.21 g (0.36 mmol) of 1-ethyl-3-methylimidazolium bis (pentafluoroethyl)fluorochlorophosphate is mixed with 2.0 g of water. After intensive stirring for about 20 min, the mixture is homogeneous. All volatile constituents are then removed in a high vacuum, leaving 0.15 g of an oil, which is analysed by spectroscopy. The $^{19}$F NMR spectrum and the $^{31}$P NMR spectrum show the formation of 1-ethyl-3-methylimidazolium bis(pentafluoroethyl)phosphinate.

NMR data:
$^{19}$F NMR spectrum, solvent-water, electronic standard (CCl$_3$F), ppm: −81.26 s (2CF$_3$), −126.42 d (2CF$_2$), $J^2_{P,F}$=77 Hz.

The invention claimed is:

1. A compound containing organofluorochlorophosphate anions, of formula (I)

[Kt]$^{z+}$z[(C$_n$H$_m$F$_{2n+1-m}$)$_x$PCl$_y$F$_{6-x-y}$]$^-$    (I)

in which [Kt]$^{z+}$ denotes an inorganic or organic cation, where n=1-12, m=0 to 2n+1, x=1-4, y=1-4, z=1-4 and with the proviso that x+y is ≦5.

2. The compound according to claim 1, wherein m=0 and y=1.

3. The compound according to claim 1, wherein x=3.

4. The compound according to claim 1, wherein n=2, 3 or 4.

5. The compound according to claim 1, wherein the compound of the formula (I) is [Kt]$^{z+}$z[(C$_2$F$_5$)$_3$PClF$_2$]$^-$, [Kt]$^{z+}$z [(C$_3$F$_7$)$_3$PClF$_2$]$^-$ or [Kt]$^{z+}$z[(C$_4$F$_9$)$_3$PClF$_2$]$^-$.

6. The compound according to claim 1, wherein [Kt]$^{z+}$ is an ammonium, phosphonium, uronium, thiouronium, guanidinium cations or heterocyclic organic cation.

7. The compound according to claim 1, wherein [Kt]$^{z+}$ is an ammonium cation, of formula (1)

[NR$_4$]$^+$    (1), where
R in each case, independently of one another, denotes
H, OR', NR'$_2$, with the proviso that a maximum of one substituent R in formula (1) is OR', NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more R may be partially or fully substituted by halogens, or partially substituted by —OH, —OR', —CN, —NR'$_2$, —C(O)OH, —C(O)NR'$_2$, —SO$_2$NR'$_2$, —C(O)X, —SO$_2$OH, —SO$_2$X, —NO$_2$, —SR', —S(O) R', —SO$_2$R' and where one or two non-adjacent carbon atoms in R which are not in the α-position may be replaced by —O—, —S—, —S(O)—, —SO$_2$—, —SO$_2$O—, —C(O)—, —C(O)O—, —N+R'$_2$—, —P(O)R'O—, —C(O)NR'—, —SO$_2$NR'—, —OP(O) R'O—, —P(O)(NR'$_2$)NR'—, —PR'$_2$=N— or —P(O) R'—where R' may be =H, non-, partially or perfluorinated C$_1$- to C$_{18}$-alkyl, C$_3$- to C$_7$-cycloalkyl, unsubstituted or substituted phenyl and X may be =halogen.

8. The compound according to claim 1, characterised in that wherein [Kt]$^{z+}$ is a phosphonium cation, of the formula (2)

[PR$^2_4$]$^+$    (2), where
R$^2$ in each case, independently of one another, denotes
H, OR' or NR'$_2$,
straight-chain or branched alkyl having 1-20 C atoms,
straight-chain or branched alkenyl having 2-20 C atoms and one or more double bonds,
straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more $R^2$ may be partially or fully substituted by halogens, or partially substituted by —OH, —OR', —CN, —NR'$_2$, —C(O)OH, —C(O)NR'$_2$, —SO$_2$NR'$_2$, —C(O)X, —SO$_2$OH, —SO$_2$X, —NO$_2$, —SR', —S(O)R', —SO$_2$R' and where one or two non-adjacent carbon atoms in $R^2$ which are not in the α-position may be replaced by —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—where R'=H, non-, partially or perfluorinated C$_1$- to C$_{18}$-alkyl, C$_3$- to C$_7$-cycloalkyl, unsubstituted or substituted phenyl and X=halogen.

9. The compound according to claim 1, wherein [Kt]$^{z+}$ is a uronium cation, of formula (3)

Where $R^3$ to $R^7$ each, independently of one another, denote

H, where H is excluded for $R^5$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents $R^3$ to $R^7$ may be partially or fully substituted by halogens, or partially substituted by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in $R^3$ to $R^7$ which are not in the α-position may be replaced by —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—where R'=H, non-, partially or perfluorinated C$_1$- to C$_{18}$-alkyl, C$_3$- to C$_7$-cycloalkyl, unsubstituted or substituted phenyl and X=halogen.

10. The compound according to claim 1, wherein [Kt]$^{z+}$ is a thiouronium cation, of formula (4)

where $R^3$ to $R^7$ each, independently of one another, denote

H, where H is excluded for $R^5$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents $R^3$ to $R^7$ may be partially or fully substituted by halogens, or partially substituted by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in $R^3$ to $R^7$ which are not in the α-position may be replaced by —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—where R'=H, non-, partially or perfluorinated C$_1$- to C$_{18}$-alkyl, C$_3$- to C$_7$-cycloalkyl, unsubstituted or substituted phenyl and X=halogen.

11. The compound according to claim 1, wherein [Kt]$^{z+}$ is a guanidinium cation, of formula (5)

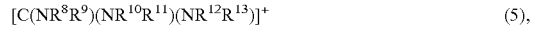

where $R^8$ to $R^{13}$ each, independently of one another, denote

H, —CN, NR'$_2$, —OR', straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents $R^8$ to $R^{13}$ may be partially or fully substituted by halogens, or partially substituted by —OH, —OR', —NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$ and where one or two non-adjacent carbon atoms in $R^8$ to $R^{13}$ which are not in the α-position may be replaced by —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—, where R'=H, non-, partially or perfluorinated C$_1$- to C$_{18}$-alkyl, C$_3$- to C$_7$-cycloalkyl, unsubstituted or substituted phenyl and X=halogen.

12. The compound according to claim 1, wherein [Kt]$^{z+}$ has formula (6)

where

HetN$^{z+}$ denotes a heterocyclic cation that is

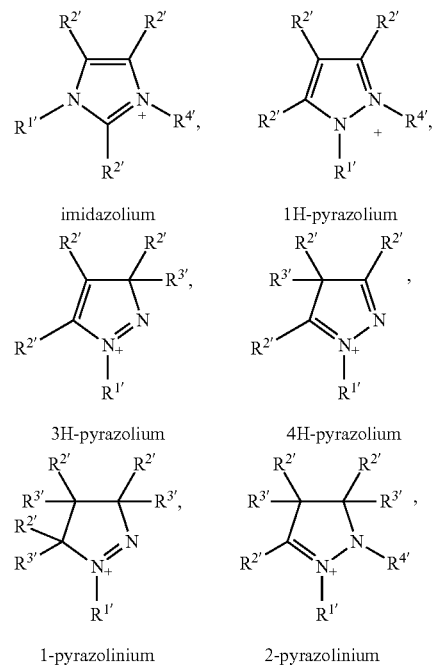

-continued 3-pyrazolinium 2,3-dihydroimidazolinium 4,5-dihydroimidazolinium 2,5-dihydroimidazolinium pyrrolidinium 1,2,4-triazolium 1,2,4-triazolium 1,2,3-triazolium 1,2,3-triazolium pyridinium pyridazinium pyrimidinium piperidinium morpholinium -continued piperazinium piperazinium pyrazinium thiazolium oxazolium indolium quinolinium isoquinolinium quinoxalinium or indolinium where the substituents R$^{1'}$ to R$^{4'}$ each, independently of one another, denote H, F, Cl, Br, I, —CN, —OR', —NR'$_2$, —P(O)R'$_2$, —P(O)(OR')$_2$, —P(O)(NR'$_2$)$_2$, —C(O)R', —C(O)OR', —C(O)X, —C(O)NR'$_2$, —SO$_2$NR'$_2$, —SO$_2$OH, —SO$_2$X, —SR', —S(O)R', —SO$_2$R' and/or NO$_2$, with the proviso that R$^{1'}$, R$^{3'}$, R$^{4'}$ are H and/or a straight-chain or branched alkyl having 1-20 C atoms, straight-chain or branched alkenyl having 2-20 C atoms and one or more double bonds, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, saturated, partially or fully unsaturated heteroaryl, heteroaryl-C$_1$-C$_6$-alkyl or aryl-C$_1$-C$_6$-alkyl, where the substituents R$^{1'}$, R$^{2'}$, R$^{3'}$ and/or R$^{4'}$ together may also form a ring system, where one or more substituents R$^{1'}$ to R$^{4'}$ may be partially or fully substituted by halogens, or by —OH, —OR', NR'$_2$, —CN, —C(O)OH, —C(O)NR'$_2$, —SO$_2$NR'$_2$, —C(O)X, —SO$_2$OH, —SO$_2$X, —SR', —S(O)R', —SO$_2$R', —NO$_2$, but where R$^{1'}$ and R$^{4'}$ cannot simultaneously be fully substituted by halogens and where, in the substituents R$^{1'}$ to R$^{4'}$, one or two non-adjacent carbon atoms which are not bonded to the heteroatom may be replaced by —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'—, where R'=H, non-, partially or perfluorinated C$_1$- to C$_{18}$-alkyl, C$_3$- to C$_7$-cycloalkyl, unsubstituted or substituted phenyl and X=halogen.

13. The compound according to claim 1, wherein [Kt]$^{z+}$ is a [(R$^o$)$_3$O]$^+$ cation or a [(R$^o$)$_3$S]$^+$ cation, where R$^o$ denotes straight-chain or branched alkyl groups having 1-8 C atoms or unsubstituted phenyl or phenyl which is substituted by R$^o$, OR$^o$, N(R$^o$)$_2$, CN or halogen.

14. The compound according to claim 1, wherein [Kt]$^{z+}$ is a metal cation.

15. The compound according to claim 14, wherein the metal cation is a metal from groups 1 to 12 of the Periodic Table.

16. The compound according to claim 14, the metal is Li, Na, K, Rb, or Cs.

17. The compound according to claim 1, that is an imidazolium, pyridinium, pyrrolidinium, ammonium, phosphonium or guanidinium salt containing a [(C$_2$F$_5$)$_3$PClF$_2$]$^-$, [(C$_3$F$_7$)$_3$PClF$_2$]$^-$ or [(C$_4$F$_9$)$_3$PClF$_2$]$^-$ anion.

18. A process for the preparation of compounds according to claim 1 containing organofluorochlorophosphate anions comprising the reaction of a chloride salt with organofluorophosphoranes.

19. A process for the preparation of a compound (I) according to claim 1 comprising reacting [Kt]$^{z+}$z[Cl]$^-$ with a compound of the general formula (II)

$$(C_nH_mF_{2n+1-m})_xPF_{5-x} \qquad (II)$$

in which [Kt]$^{z+}$ denotes an inorganic or organic cation where z=1-4, and in the compounds of the formula II n=1-12, m=0 to 2n+1, x=1-4 and y=1-4.

20. The process according to claim 19, wherein compounds of the formula II y=1 and m=0.

21. The process according to claim 19, wherein the reaction is carried out at temperatures of −40 to 180° C.

22. The process according to claim 19, wherein the reaction is carried out in a solvent.

23. The process according to claim 22, wherein the solvent is a nitrile, dialkyl carbonate, glyme, dialkyl ether, cyclic ether, dimethylformamide, dimethyl sulfoxide, dichloromethane, water or mixtures thereof.

24. A process for the preparation of organophosphinates comprising reacting a compound according to claim 1 with water or water-containing solvents or solvent mixtures.

25. The process according to claim 24, wherein the reaction is carried out at −40 to 200° C.

26. A solvent or solvent additive, phase-transfer catalyst, extractant, heat-transfer medium, surface-active substance, plasticiser, flameproofing agent, conductive salt or catalyst comprising at least one compound according to claim 1.

27. Electrolytes, electrochemical cells, capacitors or fuel cells comprising at least one compound according to claim 1.

* * * * *

UNITED STATES PATENT AND TRADEMARK OFFICE
CERTIFICATE OF CORRECTION

| | |
|---|---|
| PATENT NO. | : 8,211,277 B2 |
| APPLICATION NO. | : 12/525099 |
| DATED | : July 3, 2012 |
| INVENTOR(S) | : Nikolai Ignatyev et al. |

It is certified that error appears in the above-identified patent and that said Letters Patent is hereby corrected as shown below:

Column 20, line 21 reads: "$[(C_3F_7)_3PCIF_2]^{-\text{ or }[Kt]^{z+}} z[(C_4F_9)_3PCIF_2]^-$." should read -- $[C_3F_9)_3PCIF_2]^-$ or $[Kt]^{z+} z[(C_4F_9)_3PCIF_2]^-$. --

Signed and Sealed this
Sixth Day of November, 2012

David J. Kappos
*Director of the United States Patent and Trademark Office*